United States Patent [19]
Hensley et al.

[11] Patent Number: 5,254,748
[45] Date of Patent: Oct. 19, 1993

[54] METHYL-TERTIARY ETHER PRODUCTION

[75] Inventors: Harvey D. Hensley; Richard L. Anderson, both of Bartlesville, Okla.; Michael E. Olbrich, Naperville, Ill.

[73] Assignee: Phillips Petroleum Company, Bartlesville, Okla.

[21] Appl. No.: 809,687

[22] Filed: Dec. 17, 1991

Related U.S. Application Data

[63] Continuation of Ser. No. 577,182, Sep. 4, 1990, abandoned.

[51] Int. Cl.$^5$ .............................................. C07C 41/06
[52] U.S. Cl. .................................... 568/697; 585/314; 585/315; 585/324; 585/331; 585/332
[58] Field of Search ................ 568/697; 585/314, 315, 585/324, 331, 332

[56] References Cited

U.S. PATENT DOCUMENTS

| | | | |
|---|---|---|---|
| 3,254,023 | 5/1966 | Miale et al. | 208/120 |
| 3,522,024 | 7/1970 | Billings et al. | 48/214 |
| 4,152,365 | 5/1979 | Drehman | 585/256 |
| 4,329,516 | 5/1982 | Al-Muddarris | 568/697 |
| 4,544,777 | 10/1985 | Hutson, Jr. et al. | 568/697 |
| 4,546,204 | 10/1985 | Parris | 568/697 |
| 4,558,168 | 12/1985 | Gussow et al. | 585/324 |
| 4,754,078 | 6/1988 | Vora et al. | 568/697 |
| 4,774,364 | 9/1988 | Chou | 568/697 |
| 4,797,133 | 1/1989 | Pujado | 44/53 |
| 4,970,097 | 12/1990 | Harandi et al. | 44/77 |

Primary Examiner—Marianne M. Cintins
Assistant Examiner—Kimberly J. Kestler
Attorney, Agent, or Firm—Marianne H. Michel

[57] ABSTRACT

A method for integrating several petroleum refining processes so as to efficiently produce tertiary alkyl ether compounds from a feed stream containing both saturated and unsaturated hydrocarbons is disclosed. An important step for forming isoolefins in the integrated process involves simultaneous catalytic conversion of an isoparaffin to an isoolefin and an n-olefin to an n-paraffin in a combination hydrogenation/dehydrogenation reactor. The thus produced isoolefin is reacted with a primary alcohol to form the desired tertiary alkyl ether compound in an ether forming process. Other conversion process included in the overall integration are an isomerization process to convert n-paraffins to isoparaffins and optionally an alkylation process to convert isoparaffins and olefins to an alkylate product.

4 Claims, 4 Drawing Sheets

METHYL-TERTIARY ETHER PRODUCTION

CROSS REFERENCE TO RELATED APPLICATIONS

This is a continuation of copending application Ser. No. 07/577,182, filed Sep. 4, 1990, now abandoned.

This invention relates to method and apparatus for the production of tertiary-alkyl ether compounds by reacting an olefin and an organic hydroxy containing compound. In another aspect it relates to an integrated process which advantageously joins isoolefin production and ether production.

BACKGROUND OF THE INVENTION

It is well known that tertiary-alkyl ether compounds can be prepared by reacting a primary alcohol with an isoolefin having a double bond on a tertiary carbon atom, such as the catalytic reaction of methanol with isobutene and isopentanes to form methyl tertiary-butyl ether (MTBE) when reacting isobutene, and methyl tertiary-amyl ether (MTAE) when reacting isopentene. When ethanol is used i-n lieu of methanol, ethyl tertiary butyl ether (ETBE) and ethyl tertiary-amyl ether (ETAE) respectively, are formed.

Interest in the production of tertiary-alkyl ethers, which can be used for high octane blending components for gasoline, comes primarily from increased demand for higher octane gasoline with lower Reid vapor pressure. This demand has been stimulated by government regulations concerning the environment which restrict the use of lead as an octane improver for gasoline.

It is, therefore, an object of this invention to convert low octane high Reid vapor pressure hydrocarbons to high octane, low Reid vapor pressure organic compounds.

It is another object of this invention to provide a combination reactor for simultaneously dehydrogenating and hydrogenating a hydrocarbon feed stream containing an isoparaffin having four or five carbon atoms per molecule and a n-olefin having an equal or lesser number of carbon atoms, to a product stream containing an isoolefin and an n-paraffin.

It is a further object of this invention to provide improved method and apparatus for the commercial production of high octane blending components for gasoline.

It is a still further object of this invention to provide commercial processes which allow refiners to increase production of tertiary ethers by converting $C_4$ or $C_5$ hydrocarbons to their respective ethers.

SUMMARY OF THE INVENTION

In accordance with one aspect of this invention, there is provided a process for simultaneous hydrogenation of an olefin and dehydrogenation of a paraffin in a combination hydrogenation/dehydrogenation unit having a single reaction zone.

In a preferred embodiment, the simultaneous hydrogenation/dehydrogenation process is utilized in an integrated process which joins etherification with a companion process for forming isoolefins. In the integrated process, the isoolefin is formed in the combination hydrogenation/dehydrogenation reactor from a feed stream comprising a structural mixture of hydrocarbons. As used herein, a structural mixture of hydrocarbons comprises a mixture containing at least an n-olefin and an isoparaffin and may contain significant amounts of n-paraffin and isoolefin with a substantial portion of the constituents having four or five carbon atoms per molecule. The processes of hydrogenation/dehydrogenation and etherification are joined by reacting the isoolefin produced in the combination hydrogenation/dehydrogenation reactor with methanol or ethanol to produce a tertiary-alkyl ether compound. The integrated process comprises the steps of:

(a) passing a structurally mixed hydrocarbon feed stream containing an isoparaffin having four or five carbon atoms per molecule and an n-olefin, having a number of carbon atoms per molecule equal to or less than the corresponding isoparaffin, to a combination hydrogenation/dehydrogenation reactor;

(b) contacting the hydrocarbon feed stream with a supported Group VIII noble metal catalyst in the combination reactor under conditions sufficient for simultaneous conversion of the isoparaffin to an isoolefin and the n-olefin to an n-paraffin;

(c) withdrawing reaction product in a stream from the combination reactor and passing at least a portion of said combination reaction product stream to an ether forming reactor;

(d) providing a stream of primary alcohol containing one or two carbon atoms per molecule to said ether forming reactor; and (e) reacting said isoolefin and said primary alcohol in said ether forming reactor to form a tertiary ether compound, and withdrawing the tertiary ether compound from said ether reactor in an ether product stream.

In another aspect of the present invention there is provided an apparatus for the production of tertiary-alkyl ethers, the apparatus comprising:

(a) a combination hydrogenation/dehydrogenation reactor for simultaneous conversion of an isoparaffin to an isoolefin and an n-olefin to an n-paraffin;

(b) means for passing a hydrocarbon feed stream comprising a structural mixture of hydrocarbons to said combination reactor;

(c) means for withdrawing reaction product from the combination reactor and passing at least a portion of the reaction product to an ether forming reactor;

(d) means for providing a primary alcohol feed stream to the ether reactor, wherein the primary alcohol reacts with the isoolefin to produce a tertiary-alkyl ether compound; and (e) means for withdrawing the tertiary-alkyl ether compound from the ether forming reactor in an ether product stream.

Further aspects and additional advantages of the present invention will be apparent from the following detailed description of the preferred embodiments of the invention as illustrated by the drawings in which:

DETAILED DESCRIPTION OF THE PREFERRED EMBODIMENTS

Figure 1:
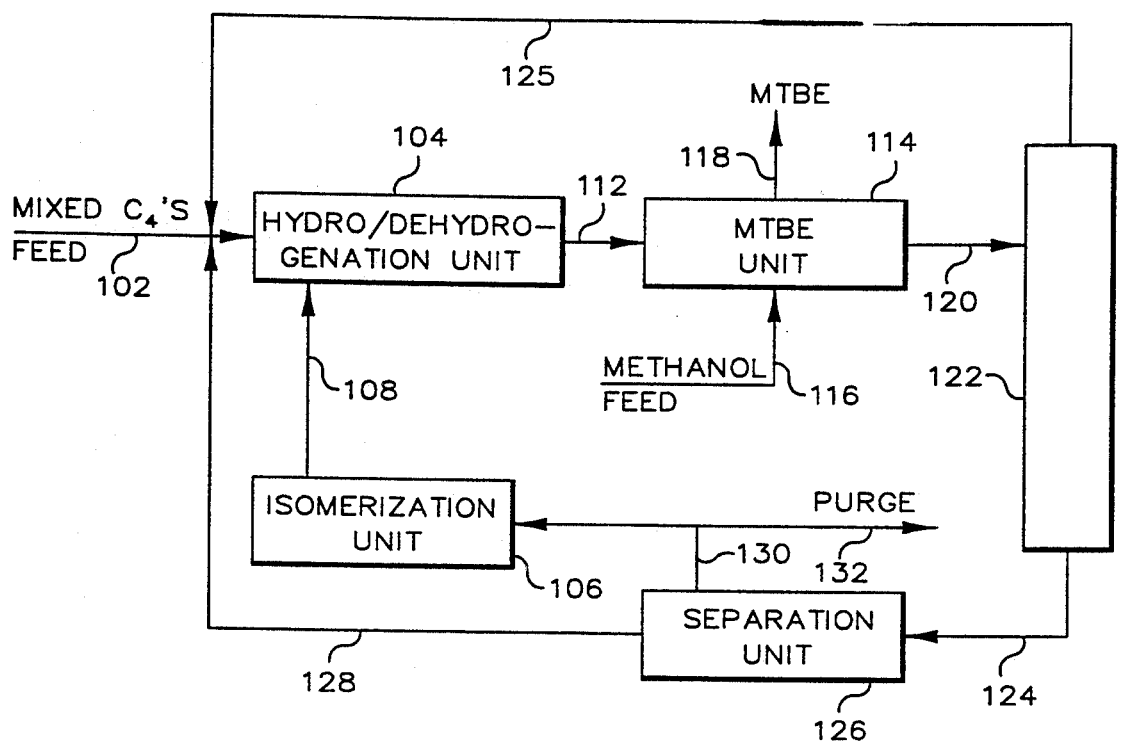
FIGS. 1 and 2 illustrate simplified process flow schemes using a combination hydrogenation/dehydrogenation process step for $C_4$ hydrocarbons in the production of MTBE or ETBE according to this invention.
Figure 2:
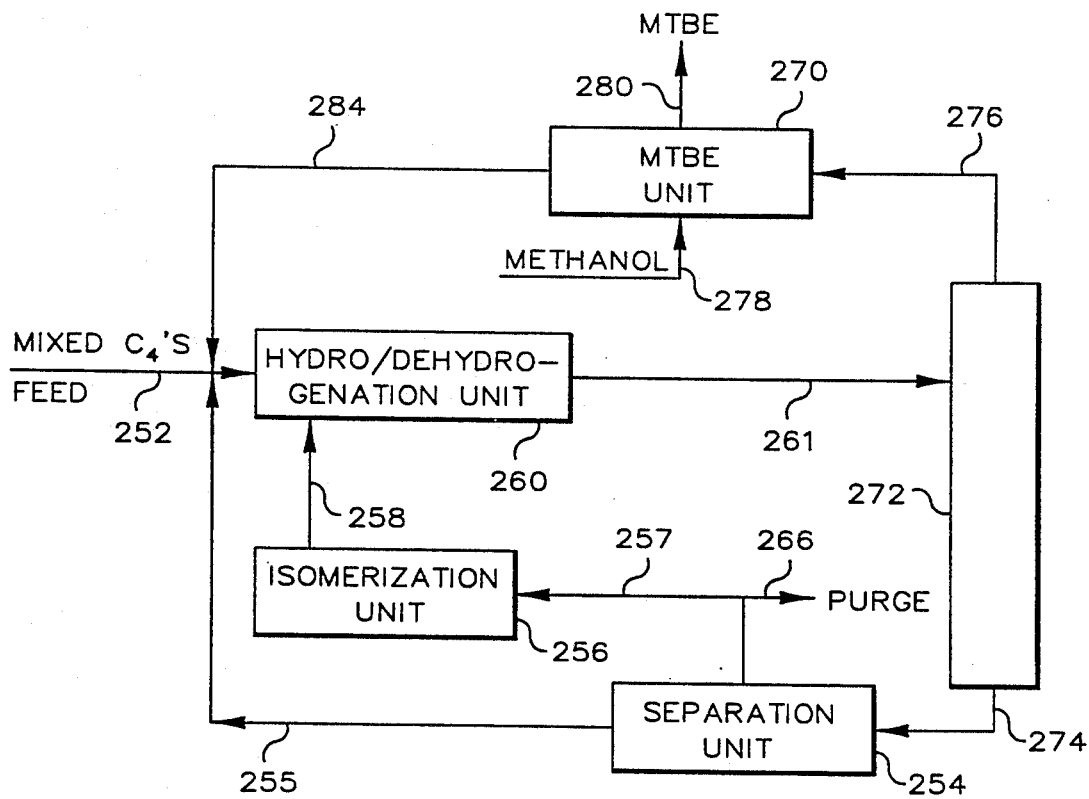

In preferred embodiments illustrated in the drawing FIGS. 1 and 2, this invention involves combinations of several processes which are employed in a unique configuration to achieve the objects of this invention. Such processes operate on a feed stream comprising a structural mixture of $C_4$ hydrocarbons, and may include distillation, absorption, and isomerization as illustrated in the specific embodiments in FIGS. 1 and 2. In other preferred embodiments illustrated in FIGS. 3–6, a variety of process configurations are disclosed in which an alkylation process step is added to the general processes disclosed in FIGS. 1 and 2, so that a portion of the mixed hydrocarbon feed stream may be converted to alkylate. In still other embodiments illustrated in FIG. 7, the feed stream comprises a mixture of $C_5$ hydrocarbons which is converted to higher octane components.

An essential feature of all the disclosed embodiments of the present invention is directed to integrating a combination hydrogenation/dehydrogenation step, which produces an isoolefin from an isoparaffin, into an etherification process. In the preferred embodiments the hydrocarbon feed material is a non-aromatic hydrocarbon having at least four carbon atoms.

The combination hydrogenation/dehydrogenation reactions are carried out in a unit having a single reaction zone, in the presence of a single dehydrogenation or reforming catalyst, such as platinum and tin on a zinc aluminate support. The catalyst composition, which is employed in the hydrogenation/dehydrogenation step of this invention, can be prepared by any suitable method, such as is well known by those familiar in the art. The preparation comprises combining, in any suitable manner, (i) a Group IIA metal aluminate spinel (i.e. aluminate spinel of Be and/or Mg and/or Ca and/or Sr and/or Ba), or a Group IIB metal aluminate spinel (i.e. aluminate spinel of Cd and/or Zn), or mixture of two or more of the above metal aluminate spinels; (ii) Group VIII metal and/or compounds thereof, and (iii) compounds of Ge and/or Sn and/or Pb.

Aluminate spinels, as referred to herein, are compounds of the formula $M(AlO_2)_2$ or $M(Al_2O_3)$ where H is a metal of Group IIA or IIB of the Periodic Table (as defined in Webster's New Collegiate Dictionary, 1977, page 852) with a valence of 2, such as Zn, Mg, Be, Ca and the like. The preparation of these aluminate spinels is described in numerous patents, such as U.S. Pat. No. 3,641,182; 3,670,044; 3,880,776; 3,894,110; and 4,152,365. In a preferred embodiment tin oxide is incorporated into the aluminate spinel. In another preferred embodiment, component (i) comprises zinc aluminate as a major component and calcium aluminate as a binder (generally present at about 5-25 wt. %).

In the presently preferred method of catalyst preparation, the metal aluminate spinel is prepared by ball-milling appropriate amounts of zinc oxide and alumina and, optionally, tin oxide (SnO and/or $SnO_2$), and calcining (preferably by beating in air) the mixture at a sufficiently higher temperature for a sufficient length of time to form the spinel. Preferably, the spinel component is used as support material, which is impregnated with component (ii) and with component (iii) in any suitable manner, either sequentially in any order, or simultaneously, as has been described in the above-cited patents.

The components of the catalyst composition generally are present at the following levels: about 80-98 weight-% of Group IIA and/or IIB metal aluminate spinel (preferably zinc aluminate); about 0.05-5 weight-% of Group VIII metal (preferably Pt); and about 0.1-5 weight-% Group IVA metal (preferably Sn which is present as an oxide). It is understood that additional components which are beneficial for catalyzing the hydrogenation/dehydrogenation operation may be present in small amounts, such as Re, Au, Ag, alkali metals, Ce, and the like. Suitable inorganic binder materials (such as amorphous alumina) may also be present. Generally, the surface area of the composition of matter (after calcination) is in the range of from about 5 to about 100 $m^2/g$ (determined by nitrogen adsorption in accordance with the BET method).

In this combination hydrogenation/dehydrogenation unit the beat evolved in the exothermicity of the butene hydrogenation reaction is balanced against the nearly equal heat absorbed in the endothermicity of the isobutane dehydrogenation reaction. The reaction in the hydrogenation/dehydrogenation unit may be represented by the following equation for a preferred embodiment:

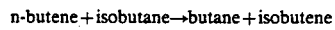

n-butene + isobutane → butane + isobutene

Of course, the reaction conditions of temperature and pressure must be such as to permit both hydrogenation and dehydrogenation reactions to proceed. It has been found that the heat requirements of the combined reaction can be essentially satisfied through internal generation with the reaction temperature generally in the range of from about 600° F. to about 1100° F. The preferred pressure is generally in the range of about 25-75 psig but can be substantially higher.

In the preferred combination hydrogenation/dehydrogenation process step, a vaporized $C_4$ hydrocarbon feed stream, optionally mixed with steam, is preheated and passed through a reactor containing a fixed bed of the catalyst composition (which can be in any suitable form such as granules, pellets, spheres and the like). The liquid hourly space velocity of the vaporized structurally mixed hydrocarbon feed (excluding steam) generally is in the range of from about 0.5-4.0. In another embodiment, a $C_5$ hydrocarbon feed stream is converted.

Referring specifically now to FIG. 1, there is illustrated a preferred embodiment of this invention in which a structurally mixed $C_4$ hydrocarbon feed stream may be converted to a tertiary alkyl ether such as MTBE (methyl tertiary-butyl ether). Depending on the concentration of isobutane in the feed stream, it may be necessary, however, to add additional isobutane from an external source to achieve full conversion of the feed stream to NTBE.

A structurally mixed $C_4$ hydrocarbon feed stream comprising n-butene, n-butane, isobutene, and isobutane from a catalytic cracking plant or other source, is provided via conduit 102 to a combination hydrogenation/dehydrogenation unit 104 along with an isobutane stream via conduit 108 supplied from an isomerization unit 106.

The reaction product from the combination hydrogenation/dehydrogenation unit 104 comprising primarily isobutene but also containing significant amounts of butene-1, butene-2, n-butane and isobutane is charged to a conventional ether forming unit such as MTBE unit 114 via conduit 112, along with methanol feed which is supplied via conduit 116. From unit 114, which includes a reactor and a distillation column, MTBE is recovered via conduit 118 for use in gasoline blends as an octane enhancer. The MTBE operation reacts isobutene with methanol to make MTBE. The ether forming reaction of the MTBE etherification process step of this invention is known in the art both generally and in many of its details. Reference is made to U.S. Pat. No. 3,846,088 in which such an ether production, particularly for the production of MTBE, is described. Also, the above-described ether forming reaction can be modified by persons having ordinary skill in the art so as to produce ethyl tertiary-butyl ether (ETBE) by employing ethanol in lieu of methanol.

A residual stream of remaining unreacted constituents, enriched in linear butenes, is withdrawn from the MTBE unit 114 via conduit 120 and is passed to a distillation tower 122. In tower 122 n-butane and butene-2 are separated from the feed mixture and withdrawn as a bottoms stream via conduit 124. An overhead distillation product comprising isobutane, isobutene and butene-1 is withdrawn from distillation tower 122 and recycled to the combination reactor 104 via conduit 125.

The distillation bottoms stream flowing in conduit 124 is passed to a separations unit 126, which may provide either an adsorption or extractive distillation step to separate n-butane and butene-2. The butene-2 fraction is withdrawn from separation unit 126 and recycled directly to the combination reactor 104 via conduit 128. n-Butane is withdrawn from separation unit 126 via conduit 130 and passed to an isomerization unit 106, where isobutane is produced therefrom. The isomerization unit 106 is a conventional catalytic unit for the conversion of n-butane to isobutane. A purge stream withdrawn from separation unit 126 via conduits 130 and 132 is needed to remove the saturates which are present in the mixed C$_4$ feed introduced via conduit 102.

The mixed C$_4$ feed stream in conduit 102 may be introduced at various other points in the process network, depending upon its composition. The feed stream in the illustrated process should be introduced into a stream having a similar composition. For example, if the mixed C$_4$ feed stream contains no iso-compounds, it should be introduced in conduit 124. If the mixed C$_4$ feed stream contains substantial isobutene, it may be introduced into the MTBE unit 114.

The embodiment of the present invention illustrated in FIG. 2 employs units which operate in the same manner as the corresponding units in FIG. 1, and the process flow illustrated in FIG. 2 differs only slightly from that of FIG. 1. Referring now to FIG. 2, a structurally mixed C$_4$ hydrocarbon feed stream comprising n-butene, n-butane, isobutene, and isobutane from a catalystic cracking plant or other source, is provided via conduit 252 to a combination hydrogenation/dehydrogenation unit 260, along with an isobutane stream via conduit 258 supplied from an isomerization unit 256. The effluent from the hydrogenation/dehydrogenation unit 260 feeds the distillation column 272 via conduit 261 instead of feeding to the MTBE unit as illustrated in FIG. 1. The overhead from the distillation unit 272 in FIG. 2, which is enriched in isobutene and also contains isobutane and butene-1, is then fed to the MTBE unit 270 via conduit 276 along with methanol feed which is supplied via conduit 278. In the MTBE unit 270, MTBE is produced and separated via conduit 280, and the unreacted C$_4$'s are recycled to hydrogenation/dehydrogenation unit 260 via conduit 284. The remainder of the process flow including flow through separation unit 254 via conduit 274, then through isomerization unit 256 via conduit 257 and recycle streams via conduits 284 and 255 is identical to the process flow illustrated in FIG. 1. As stated above in reference to FIG. 1, the mixed C$_4$ feed stream in FIG. 2 is preferably introduced into a stream with a composition most resembling the composition of the mixed C$_4$ feed stream.

The processes illustrated in FIGS. 1-2 generally require a purge of saturated compounds essentially equivalent to the amount of saturated compounds present in the mixed C$_4$ feed stream. A purge stream withdrawn from separation unit 254 via conduit 266 is needed to remove the saturates which are present in the mixed C$_4$ feed introduced via conduit 252. Total utilization of the mixed C$_4$ feed stream for octane improvement can be accomplished by the addition of an alkylation unit to the process schemes illustrated in FIGS. 1 and 2. Example configurations are shown in FIGS. 3-6.

The alkylation unit illustrated in FIGS. 3-6 is well known. U.S. Pat. Nos. 3,213,157, 3,211,536, and 3,309,882 describe such alkylation processes which employ liquid hydrofluoric (HF) acid as the catalyst. These patents are incorporated herein by reference. In the conventional HF alkylation reaction liquid isoparaffin and liquid olefin are contacted with liquid HF catalyst to form a reaction mixture. After liquid-liquid phase separation of this reaction mixture an alkylate is removed from the organic phase as one product of the process. The olefins useful in HF alkylation reactions are those having three to five carbon atoms. The paraffins used for alkylation reaction are generally isoparaffins having four to six carbon atoms, isobutane being particularly preferred.

Figure 3:
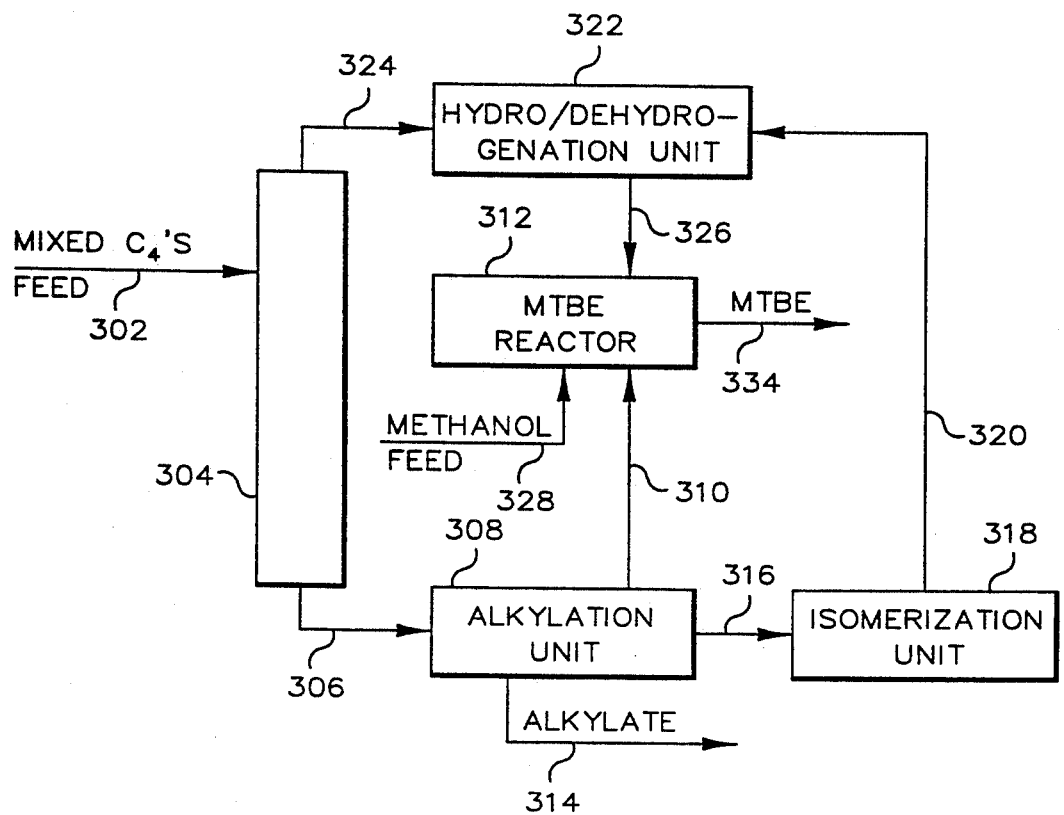
FIGS. 3–6 illustrate simplified process flow schemes using a combination hydrogenation/dehydrogenation process step for $C_4$ hydrocarbons in the production of MTBE or ETBE and alkylate according to this invention.

Referring now to FIG. 3, a feed stream identical to the feed stream described in reference to FIG. 1 is provided to distillation tower 304 via conduit 302. In distillation tower 304 n-butane and butene-2 are separated from the feed mixture and withdrawn in a bottoms stream and passed via conduit 306 to an alkylation unit 308. Also introduced into the alkylation unit 308 via conduit 310 is an isobutane, butene-1 and butene-2 containing stream from an ether forming unit such as MTBE unit 312. From the alkylation unit an alkylate product stream is withdrawn via conduit 314 and a paraffin (n-butane) stream is withdrawn via conduit 316. The n-paraffin stream in conduit 316 is passed to an isomerization unit 318 where the n-butane is converted to isobutane. The isomerization reaction product stream containing isobutane flowing in conduit 320 is passed to the combination hydrogenation/dehydrogenation 322 via conduit 320. Also introduced into the hydrogenation/dehydrogenation unit 322, is an overhead distillation product comprising isobutane, isobutene and butene-1 which, is withdrawn from distillation tower 304 via conduit 324. enriched in isobutene, is withdrawn from the combination hydrogenation/dehydrogenation unit 322 and passed to the MTBE unit 312 via conduit 326, where isobutene is reacted with methanol supplied via conduit 328 to form MTBE. If ethanol is charged in lieu of methanol, ETBE is formed in unit 312. From unit 312, MTBE is withdrawn via conduit 334, and a residual stream of remaining unreacted constituents is withdrawn via conduit 310 and passed to alkylation unit 308.

Figure 4:
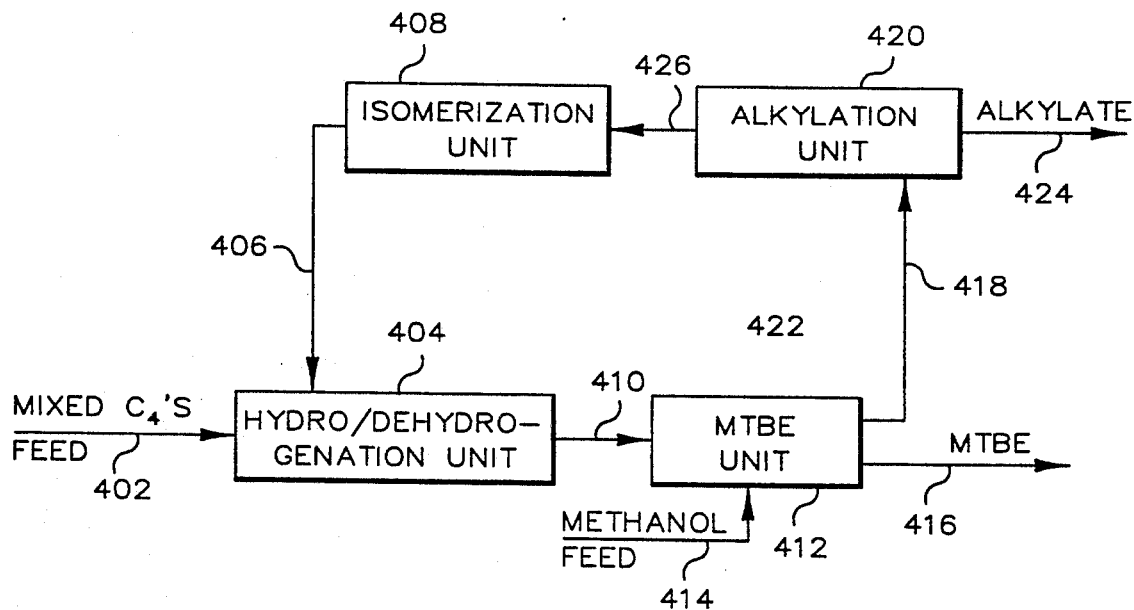

Referring now to FIG. 4, a feed stream, identical to the feed stream described in reference to FIG. 1, is provided to a combination hydrogenation/dehydrogenation unit 404 via conduit 402. Also charged to combination unit 404 via conduit 406 is an isobutane containing stream supplied from the isomerization unit 408. Reaction products comprising isobutene and n-butane along with unreacted n-butene and isobutane are withdrawn from combination unit 404 via conduit 410 and passed to an ether forming unit such as MTBE unit 412. In MTBE unit 412 isobutene is reacted with methanol supplied via conduit 414 to produce MTBE. From unit 412, MTBE product is withdrawn via conduit 416, and a residual stream of remaining unreacted constituents comprising essentially n-butane, and n-butenes and isobutane are withdrawn via conduit 418 and passed to the alkylation unit 420. From alkylation unit 420 an alkylate product is withdrawn via conduit 424, and n-butane is withdrawn via conduit 426 and passed to isomerization unit 408.

Figure 5:
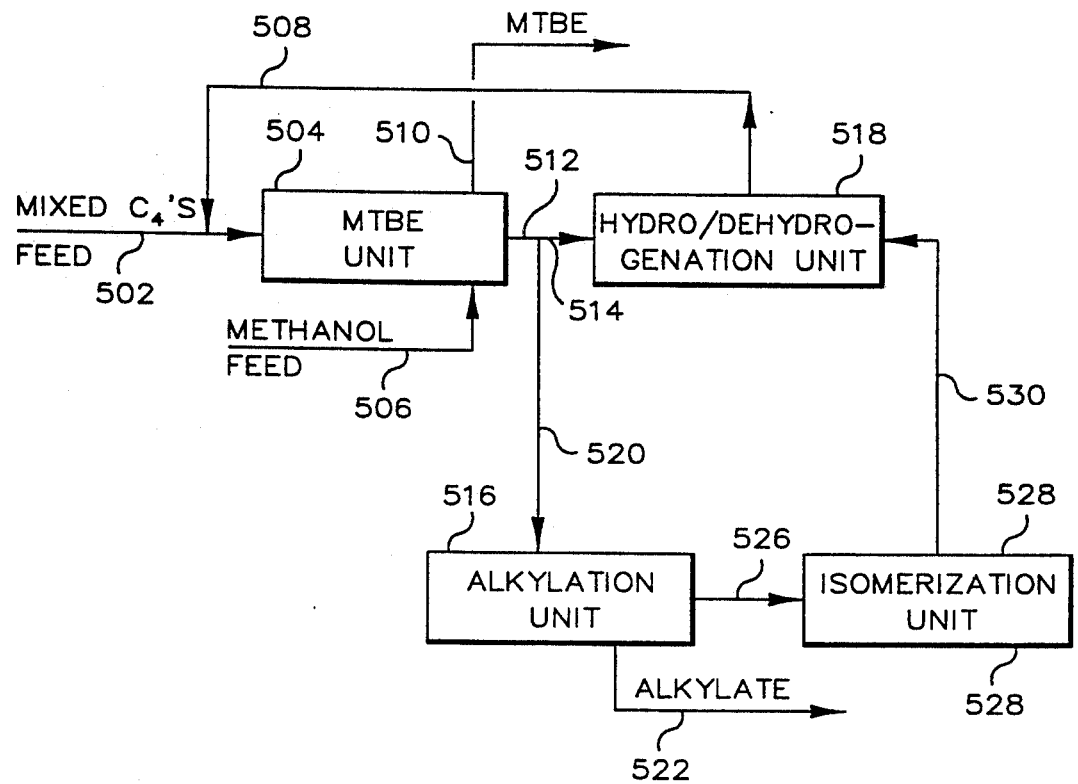

Referring now to FIG. 5, a feed stream identical to the feed stream described in reference to FIG. 1 is provided to an ether forming reactor such as NTBE unit 504 via conduit 502. Also charged to the MTBE unit 504 via conduit 506 is a methanol feed stream, and a recycle stream via conduit 508 enriched in isobutene. The isobutene and methanol are reacted in unit 504 to produce NTBE which is withdrawn via conduit 510. Also withdrawn from unit 504 is a stream containing n-butene and isobutane via conduit 512. The stream flowing in conduit 512 is divided with a first portion passed to a hydrogenation/dehydrogenation unit 518 via conduit 514, and a second portion passed to an alkylation unit 516 via conduit 520. Alkylate is withdrawn from alkylation unit 516 via conduit 522, and n-butane is withdrawn via conduit 526. The n-butane flowing in conduit 526 is passed to an isomerization unit 528 where the n-butane is converted to isobutane and then passed to the combination unit 518 via conduit 530.

Figure 6:
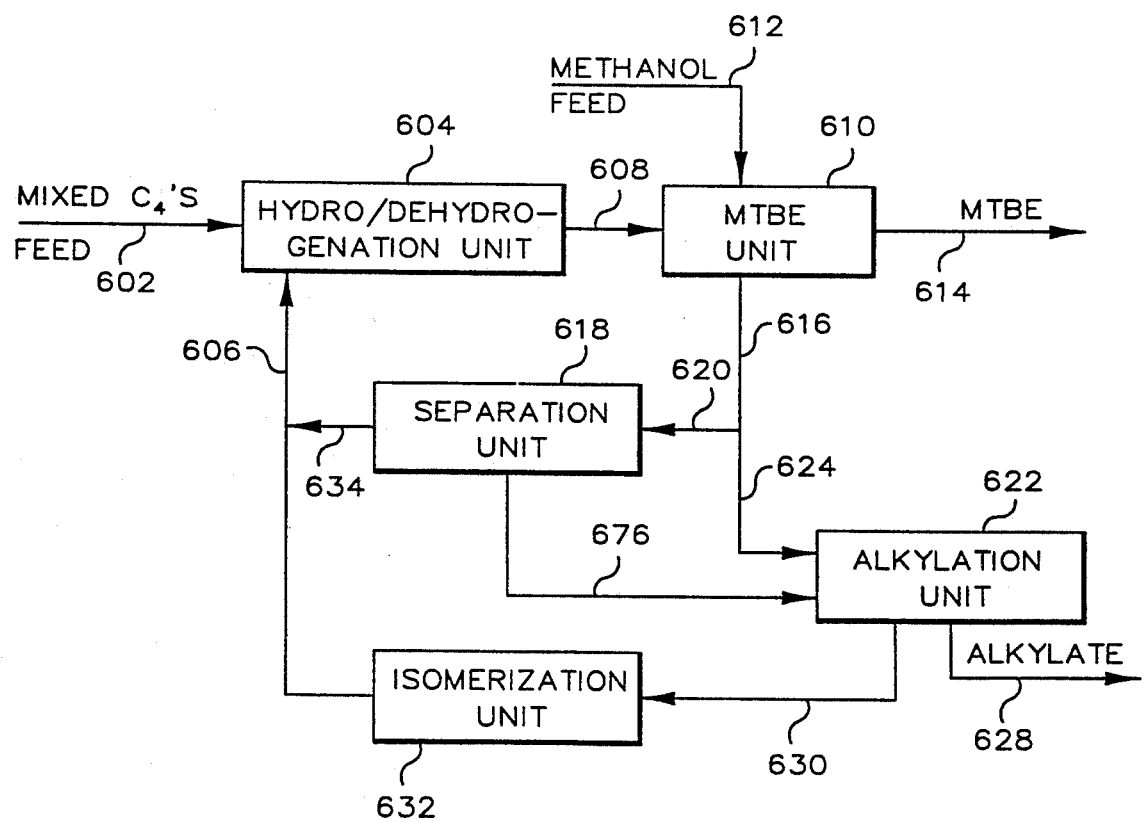

Referring now to FIG. 6, a feed stream identical to the feed stream described in reference to FIG. 1 is provided to a combination hydrogenation/dehydrogenation unit 604 via conduit 602. Also charged to the combination unit 604 via conduit 606 is a recycle stream containing isobutane and n-butene. The product stream containing isobutene, isobutane, n-butane and n-butene is withdrawn from the combination unit 604 and passed to an ether forming unit such as MTBE unit 610 via conduit 608. A methanol feed stream is also provided to MTBE unit 610 via conduit 612. From MTBE unit 610 MTBE product is withdrawn via conduit 614, and a residual stream of remaining unreacted constituents containing n-butene, n-butane, and isobutane is withdrawn via conduit 616. The stream flowing in conduit 616 is divided so that a first portion is passed to a separation unit 618 via conduit 620, and a second portion is passed to alkylation unit 622 via conduit 624. Olefins are separated from paraffins in separation unit 618 and a paraffins stream comprising n-butane and isobutane is withdrawn from separation unit 618 and passed to alkylation unit 622 via conduit 626.

Alkylate product is withdrawn from alkylation unit 622 via conduit 628. Also withdrawn from alkylation unit 622 via conduit 630 is a stream comprising n-butane which is passed to isomerization unit 632. The n-butane is isomerized in isomerization unit 632 and withdrawn therefrom and recycled to the combined unit 604 via conduit 606. Now referring again to separation unit 618, the olefin stream comprising n-butene's and isobutene is withdrawn from separation unit 618 and recycled to the combination hydrogenation/dehydrogenation unit 604 via the combination of conduits 634 and 606.

Figure 7:
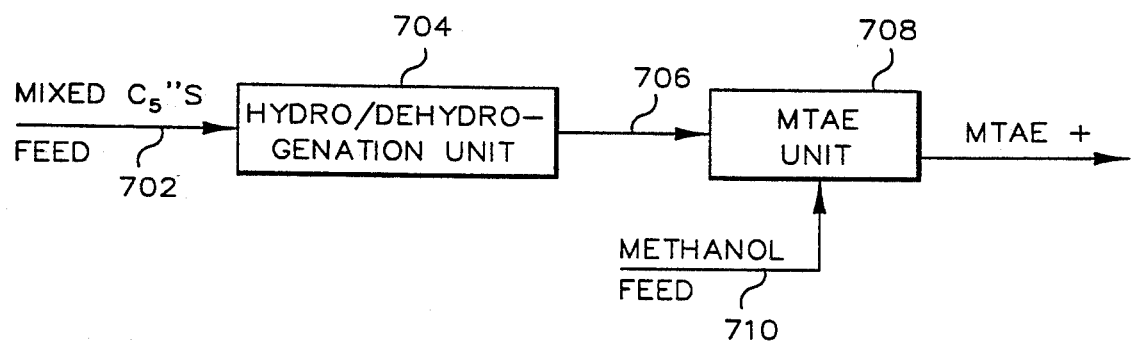
FIG. 7, illustrates a simplified process flow scheme using a combination hydrogenation/dehydrogenation process step for $C_5$ hydrocarbons in the production of NTAE or ETAE according to this invention.

Referring now to FIG. 7, a structurally mixed $C_5$ feed stream primarily comprised of n-pentene and also containing isopentane and n-pentane is provided to a combination hydrogenation/dehydrogenation unit 704 via conduit 702. The reaction product from the combination unit 704 comprising primarily isopentene and also containing isopentane, n-pentane and n-pentene is passed to an ether forming unit such as MTAE unit 708 via conduit 706. In MTAE unit 708 isopentene is reacted with methanol, which is provided to reactor 708 via conduit 710, to form MTAE product. If ethanol is provided in lieu of methanol ethyl tertiary-amyl ether (ETAE) is formed in unit 708. The MTAE or ETAE product is withdrawn from reactor 708 along with unreacted isopentene and methanol, and n-pentene, isopentane and n-pentane.

Other possible process configurations for the conversion of a mixed $C_5$ stream to MTAE or ETAE can be illustrated by replacing the MTBE units in FIG. 1 and FIG. 2 with either MTAE or ETAE units. In these processes the mixed $C_5$ feed can be introduced where desired. The normal, saturated $C_5$ compounds in the mixed $C_5$ feed are purged from the loop via conduit 132 in FIG. 1, or via conduit 266 in FIG. 2.

The following examples illustrate the combination hydrogenation/dehydrogenation step, which is considered to be the critical step in each of the disclosed embodiments. These examples are presented in further illustration of this invention and are not to be considered as unduly limiting the scope of this invention.

EXAMPLE 1

A blend of technical grade isobutane with research grade butene-1 was introduced into a pilot plant reactor having a length of about 2 ft. and a diameter of about 2 inches. The reactor was filled with a layer (about 14 inches high) containing about 974 grams (780 cc) of a dehydrogenation catalyst comprising platinum and tin on a zinc aluminate/calcium aluminate base. The catalyst was prepared substantially in accordance with the method described in Example I of U.S. Pat. No. 4,152,365, and contained about 0.6 weight-% platinum, 1.0 weight-% tin 98.4 weight-% zinc aluminate/calcium aluminate. The feed blend comprised the following composition:

| isobutane | 47.79% by weight, |
| n-butane | 1.56% by weight, |
| n-butene-1 | 49.99% by weight, |
| trans-2-butene | 0.10% by weight, |
| cis-2-butene | 0.02% by weight, |
| propane | 0.19% by weight, |
| pentane | 0.02% by weight, and |
| air | 0.34% by weight |

A hydrocarbon feed stream composed of the above feed blend was contacted with the above-described catalyst in the pilot plant reactor. Generally the feed stream was passed through the reactor, both with and without steam, for a period of time required to essentially achieve equilibrium conditions. Then the hydrocarbon feed to the reactor was discontinued, the reactor was purged with steam for 5 minutes, and air was introduced into the reactor for 25 minutes at a rate of about 10 SCFH and then for 25 minutes at a rate of about 20 SCFH with steam flow at about 2125-g/hr, so as to regenerate the hot catalyst by burning off coke deposits. Thereafter, the flow of air was discontinued and pure steam was passed through the reactor for 5 minutes before beginning the next experimental run.

For analyzing reaction products, the reactor effluent was cooled to ambient temperature (about 77° F.), and the uncondensed gaseous effluent was analyzed by gas chromatography. The main component of the uncondensed effluent was isobutene. Reactor conditions and test results demonstrated high isobutane conversion and high selectivity to isobutene, and also high butene-1 conversion and high selectivity to n-butane as shown below:

|  | Run 1 | Run 2 |
|---|---|---|
| Steam flow (grams/hr.) | 1200 | — |
| Hydrocarbon flow (cc/hr) | 3080 | 400 |
| LHSV | 4.1 | 0.54 |
| Stm./HC ratio | 2.1 | — |
| Temperature (Deg. °F.) | 1100 | 850 |
| Pressure (psig) | 250 | 75 |
| Isobutane Conversion (%) | 50.4 | 18.2 |
| Selectivity to Isobutene (%)[1] | 91.1 | 88.5 |
| Run time (minutes) | 18 | 124 |
| Butene-1 conversion (%) | 82.3 | 91.6 |
| Selectivity to n-Butane (%)[2] | 29.5 | 74.1 |

[1]Yield of isobutene divided by conversion of isobutane × 100.
[2]Yield of n-butane divided by conversion of butene-1 × 100.

EXAMPLE 2

The same experimental setup and procedure as in example 1, was used with a hydrocarbon feed stream composed as follows:

| isobutane | 57.77% by weight, |
|---|---|
| n-butane | 2.00% by weight, |
| n-butene-1 | 39.25% by weight, |
| trans-2-butene | 0.05% by weight, |
| cis-2-butene | 0.00% by weight, |
| propane | 0.20% by weight, |
| pentane | 0.03% by weight, and |
| air | 0.70% by weight |

Reactor conditions and obtained test results were as follows.

| Steam flow (grams/hr.) | — |
|---|---|
| Hydrocarbon flow (cc/hr) | 400 |
| LHSV (cc/cc catalyst/hr) | 0.53 |
| Steam/HC ratio | — |
| Temperature (Deg. °F.) | 875 |
| Pressure (psig) | 75 |
| Isobutene conv. (%) | 11.2 |
| Selectivity to Isobutane (%) | 81.1 |
| Run time (minutes) | 57 |
| Butene-1 conversion (%) | 93.6 |
| Selectivity to n-Butane (%) | 75.6 |

The above test results show that the Pt, Sn on ZnAl$_2$O$_4$/CaAl$_2$O$_4$ is effective for simultaneously carrying out the required hydrogenation and dehydrogenation reactions in a single reaction zone. The hydrogen from the isobutane dehydrogenation was mostly consumed, as desired, by the hydrogenation of the linear butenes. This approach is highly advantageous because the high endothermicity of the dehydrogenation reaction can be balanced against the nearly equal exothermicity of the hydrogenation reaction, with most of the heat requirements satisfied through internal generation.

Reasonable variations, modifications and adaptations for various usages and conditions can be made within the scope of the disclosure and the appended claims, without departing from the scope of this invention.

That which is claimed is:

1. An integrated process for producing tertiary alkyl ether compounds which joins isoolefin production and ether production by reacting a produced isoolefin with a primary alcohol under etherification conditions, said integrated process comprising the steps of:

(a) passing a structurally mixed hydrocarbon feed stream containing an isoparaffin having four or five carbon atoms per molecule and an n-olefin, having a number of carbon atoms per molecule equal to said isoparaffin, to a combination hydrogenation/-dehydrogenation unit reaction zone;

(b) contacting said mixed hydrocarbon feed stream with a supported Group VIII nobel metal catalyst in said combination unit reaction zone under conditions sufficient for simultaneous conversion of a portion of said isoparaffin to an isoolefin and a portion of said n-olefin to an n-paraffin;

(c) withdrawing a reaction product stream from said combination unit reaction zone and passing at least a portion of said reaction product stream comprising at least a portion of said isoolefin to an ether forming unit reaction zone;

(d) providing a primary alcohol containing one or two carbon atoms per molecule to said ether forming unit reaction zone via an alcohol feed stream; and (e) reacting said isoolefin and said primary alcohol in said ether forming unit reaction zone under conditions sufficient to form tertiary alkyl ether and unreacted constituents and withdrawing said tertiary alkyl ether from said ether forming unit reaction zone in an ether product stream;

wherein said isoparaffin is isobutane and said n-olefin is n-butene and said ether unit reaction zone is a methyl tertiary-butyl ether unit reaction zone and said tertiary alkyl ether is methyl tertiary-butyl ether;

wherein said structurally mixed feed stream to said combination unit reaction zone, containing isobutene, said isobutane, and butene-1, is formed by separating and withdrawing a bottom stream containing n-butane and butene-2 from a source stream in a distillation tower and withdrawing said structurally mixed feed stream containing said isobutene, said isobutane and said butene-1 in an overhead stream from said distillation tower, said process additionally comprising:

contacting said bottom stream containing n-butane and butene-2 from said distillation tower with an acid catalyst under alkylation conditions in an alkylation unit reaction zone to produce reaction constituents comprising alkylate produce and n-butane;

separating said withdrawing an alkylate product stream and an n-butane stream from said alkylation unit reaction zone;

recovering said alkylate product stream;

passing said n-butane stream to an isomerization unit reaction zone wherein n-butane is isomerized to isobutane; and withdrawing a recycle stream comprising said isobutane from said isomerization unit and passing said recycle stream to said combination unit reaction zone.

2. A process in accordance with claim 1 additionally comprising:

withdrawing a residual stream of remaining unreacted constituents from said methyl tertiary-butyl ether unit reaction zone and passing said residual stream containing isobutane, n-butene, and n-butane to an alkylation unit reaction zone;

contacting said residual stream with an acid catalyst under alkylation conditions in said alkylation unit reaction zone to produce reaction constituents comprising alkylate product and n-butane;

withdrawing an alkylate product stream and an n-butane stream from said alkylation unit reaction zone;

passing said n-butane stream to an isomerization unit reaction zone wherein n-butane is isomerized to isobutane; and withdrawing a recycle stream comprising isobutane from said isomerization unit reaction zone and passing said recycle stream to said combination ii-nit reaction zone.

3. A process in accordance with claim 1 additionally comprising the following steps:

withdrawing a residual stream of remaining unreacted constituents from said methyl tertiary-butyl ether unit reaction zone;

passing a first portion of said residual stream to a separation unit and passing a second portion of said residual stream to an alkylation unit reaction zone;

separating n-butene from said first portion of said residual stream in said separation unit;

withdrawing said n-butene from said separation unit and passing said n-butene in a first recycle stream to said combination unit reaction zone;

contacting said second portion of said residual stream with an acid catalyst under alkylation conditions in said alkylation unit reaction zone to produce reaction constituents comprising alkylate product and n-butane;

withdrawing an alkylate product stream and an n-butane stream from said alkylation unit reaction zone;

passing said n-butane stream to an isomerization unit reaction zone wherein n-butane is isomerized to isobutane; and withdrawing a second recycle stream comprising isobutane from said isomerization unit reaction zone and passing said second recycle stream to said combination unit reaction zone.

4. An integrated process for producing tertiary alkyl ether compounds which joins isoolefin production and ether production by reacting an isoolefin with a primary alcohol under etherification conditions, said integrated process comprising the steps of:

(a) passing a structurally mixed hydrocarbon feed stream containing an isoolefin having four or five carbon atoms per molecule to an ether forming unit reaction zone;

(b) providing a primary alcohol containing one or two carbon atoms per molecule to said ether forming unit reaction zone via an alcohol feed stream;

(c) reacting said isoolefin and said primary alcohol in said ether forming unit reaction zone under conditions sufficient to form tertiary alkyl ether and unreacted constituents and withdrawing said tertiary alkyl ether from said ether forming unit reaction zone in an ether product stream;

(d) withdrawing a residual stream of remaining unreacted constituents comprising isoparaffin, isoolefin, n-paraffin and n-olefin having four or five carbon atoms;

(e) passing a first portion of said residual stream to a combination hydrogenation/dehydrogenation unit reaction zone;

(f) contacting said said first portion of said residual stream with a supported Group VIII noble metal catalyst in said combination unit reaction zone under conditions sufficient for simultaneous conversion of a portion of said isoparaffin to an isoolefin and a portion of said n-olefin to an n-paraffin;

(g) withdrawing a reaction product stream from said combination unit reaction zone and passing at least a portion of said reaction product stream comprising at ].east a portion of said isoolefin to an ether forming unit reaction zone;

(h) withdrawing a second portion of said residual stream from said ether forming unit reaction zone and passing said second portion to an alkylation unit reaction zone;

(i) contacting said second portion of said residual stream with an acid catalyst tinder alkylation conditions in an alkylation zone to produce reaction constituents comprising alkylate product and n-butane;

(j) withdrawing an alkylate product stream and an n-butane stream from said alkylation zone;

(k) passing said n-butane stream to an isomerization unit for converting n-butane to isobutane; and (l) withdrawing a recycle stream comprising isobutane from said isomerization unit and passing said recycle stream to said combination unit reaction zone.

* * * * *

UNITED STATES PATENT AND TRADEMARK OFFICE
CERTIFICATE OF CORRECTION

PATENT NO. : 5,254,748
DATED : October 19, 1993
INVENTOR(S) : Harvey D. Hensley, Richard L. Anderson & Michael E. Olbrich It is certified that error appears in the above-identified patent and that said Letters Patent is hereby corrected as shown below:

Column 10, line 35, delete "nobel" and insert --- noble ---

Column 11, line 9, delete "said" and insert --- and --- therefor.

Column 11, line 40, delete "ii-nit" and insert --- unit -- therefor.

Column 12, line 42, delete "].east" and insert --- least --- therefor.

Column 12, line 49, delete "tinder" and insert --- under --- therefor.

Signed and Sealed this

Fifth Day of April, 1994

Attest:

BRUCE LEHMAN

Attesting Officer     Commissioner of Patents and Trademarks